United States Patent [19]
Owens

[11] Patent Number: 4,721,115
[45] Date of Patent: Jan. 26, 1988

[54] DIAGNOSTIC CATHETER FOR MONITORING CARDIAC OUTPUT

[75] Inventor: Robert C. Owens, Forest Lake, Minn.

[73] Assignee: Cardiac Pacemakers, Inc., St. Paul, Minn.

[21] Appl. No.: 833,244

[22] Filed: Feb. 27, 1986

[51] Int. Cl.$^4$ .............................................. A61B 5/02
[52] U.S. Cl. ...................................... 128/713; 604/96
[58] Field of Search ............... 128/642, 668, 670, 672, 128/673, 691, 692, 693, 695, 713, 772; 604/96, 97, 98, 99, 282

[56] References Cited

U.S. PATENT DOCUMENTS

| | | | |
|---|---|---|---|
| 3,995,623 | 12/1976 | Blake et al. | 128/642 |
| 4,003,369 | 1/1977 | Heilman et al. | 128/772 |
| 4,328,806 | 5/1982 | Cooper | 604/99 |
| 4,380,237 | 4/1983 | Newbower | 128/693 |
| 4,508,103 | 4/1985 | Calisi | 128/673 |
| 4,572,206 | 2/1986 | Geddes et al. | 128/713 |
| 4,587,975 | 5/1986 | Salo et al. | 128/693 |
| 4,632,125 | 12/1986 | Lebler | 128/713 |

*Primary Examiner*—William E. Kamm
*Attorney, Agent, or Firm*—Orrin M. Haugen; Thomas J. Nikolai; Frederick W. Niebuhr

[57] ABSTRACT

A multi-lumen catheter having a balloon-like expander located at the distal end thereof, the interior of the balloon communicating with one of the plural lumens whereby a fluid introduced at the proximal end of the catheter can be made to inflate the balloon. A series of surface electrodes are axially spaced over a zone located near the distal end of the catheter body. Electrical conductors connected to each of the surface electrodes pass through another lumen to an electrical connector at the proximal end of the catheter. A pair of stiffener members, one being co-extensive with the zone of the catheter bearing the axially spaced surface electrodes and the other being spaced a short predetermined distance proximally of the first stiffener member are in another lumen. The gap between the two stiffener members allows the catheter to bend without kinking the lumens so that, when used, the most proximal ring electrode will be disposed near the apex of the right ventricle with the portion distal of the bend extending upward through the outflow tract of the right ventricle. Further lumens and ports communicating therewith may be added to permit the catheter to be used to take thermal dilution measurements of cardiac outputs.

7 Claims, 10 Drawing Figures

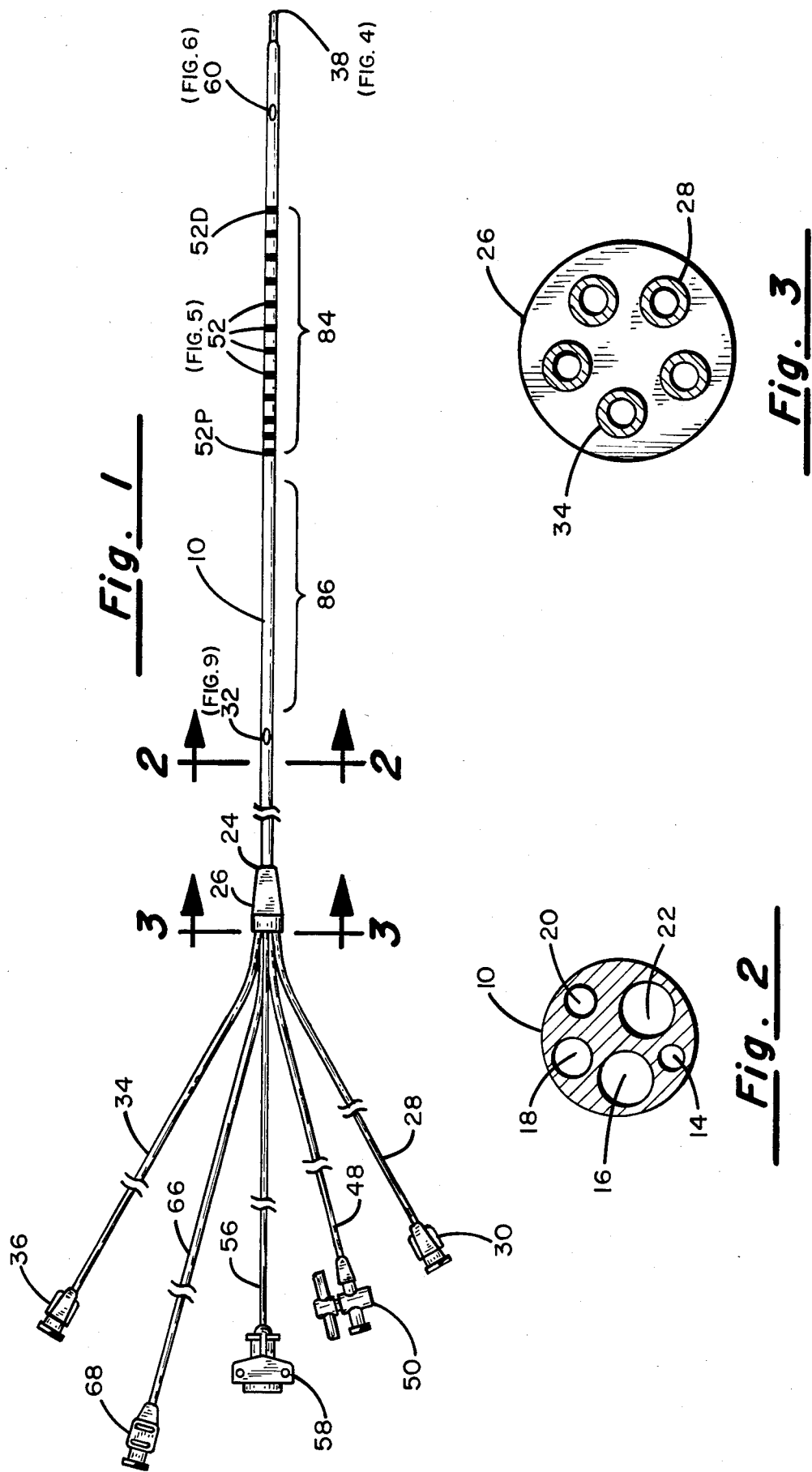

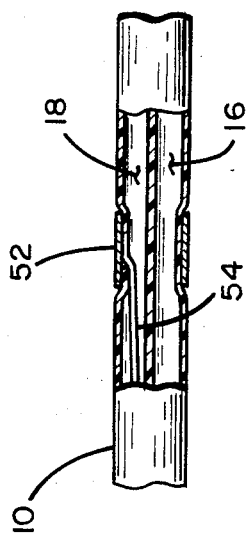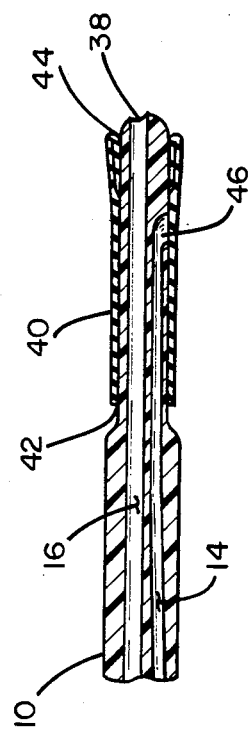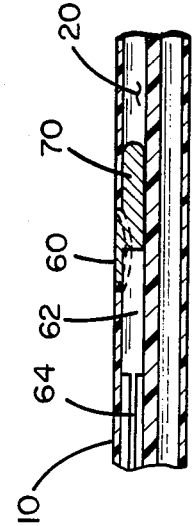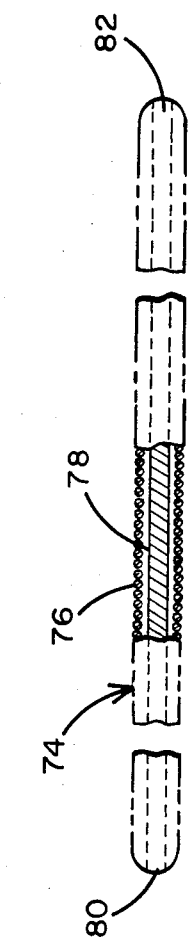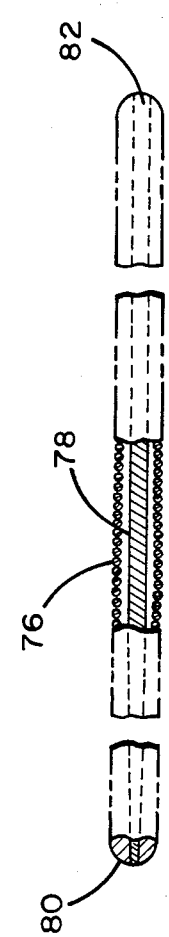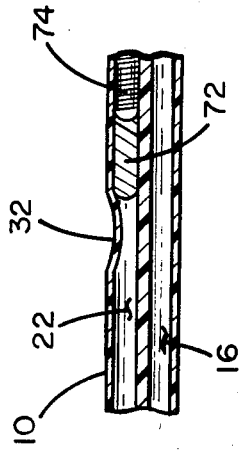

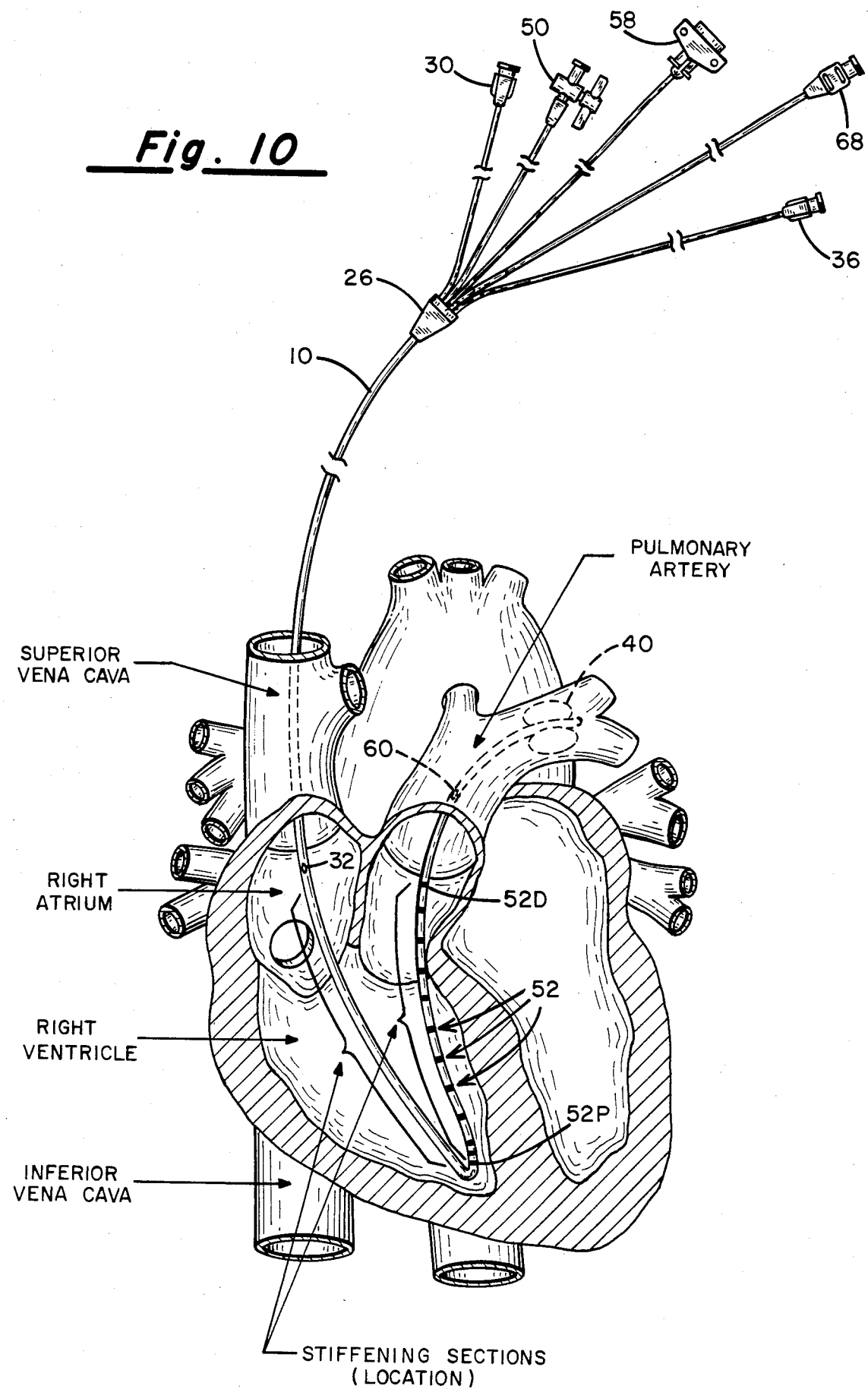

DIAGNOSTIC CATHETER FOR MONITORING CARDIAC OUTPUT

BACKGROUND OF THE INVENTION

1. Field of the Invention

This invention relates generally to medical apparatus for measuring characteristics of an animal heart, and more particularly to a diagnostic catherer to be used with appropriate equipment whereby cardiac outputs can be monitored on a beat-by-beat basis over a prolonged period of time.

2. Discussion of the Prior Art

In assessing cardiac performance and in diagnosing heart abnormalities, an important parameter to be observed is cardiac output, which is generally measured in terms of liters-per-minute and which corresponds to the heart's stroke volume multiplied by heart rate. For example, following the occurrence of a cardiac infact, the attending cardiologist may want to assess the amount of damage in terms of the heart's ability to pump blood. Also, when certain drugs are administered, the attending physician will want to monitor the effects of such drugs on cardiac performance.

Various methods are known in the art for measuring cardiac output. A common approach has been the use of a thermal dilution technique in which a catherer is used to inject cold saline solution into the heart and further means are provided on the catheter for sensing temperature at a point exterior to the heart, usually in the pulmonary outflow tract. By its very nature, the procedure can only be used on an intermittent basis at relatively widely spaced intervals. The thermal dilution technique is not capable of providing real-time data on a beat-by-beat basis.

More recently, researchers have found a way to measure stroke volume through the use of a technique called impedance pleythsmography. Here, a catherer having a plurality of surface electrodes is inserted into the right ventricle and an AC voltage is applied across one pair of space-apart surface electrodes, which may be referred to as the drive pair. At the same time, voltage signals are sensed at intermediate pairs of sensing electrodes and it is found that these signals are proportional to the impedance between the sensing electrodes, which impedance is a function of the quantity of blood contained in the heart chamber between the sensing electrodes in question. The beating action of the heart thus modulates the applied AC carrier signal and, using available signal processing techniques, the modulating signal can be removed from the carrier and it is found to be proportional to stroke volume.

Those readers desiring more information on the impedance pleythsmography technique are referred to the co-pending application of Rodney Salo et al, application Ser. No. 362,903, filed Mar. 29, 1982. Now U.S. Pat. No. 4,686,987 which is assigned to the assignee of the instant application, as well as to the published references cited therein.

The present invention is concerned with the design of a special-purpose catherer which has been developed to facilitate the real-time monitoring of stroke volume and, therefore, cardiac outputs using the impedance plethsmography technique. Specifically, the catheter has been designed to facilitate the positioning of the driving and sensing electrode pairs within the ventricular chamber of the heart in such an orientation that accurate readings can be insured. The catherer is designed so that it will be disposed in the right ventricle with a drive electrode located in the apex and with another drive electrode being located near the pulmonic valve and with the intermediate sensing electrodes spaced away from the endocardial tissue improving the quality of the intracardiac impedance signals and minimizing cardiac induced PVCs. The construction thus reduces the risk of catheter-induced arrhythmias and allows the catheter to remain in place for prolonged periods while providing the physical placement of electrodes necessary for accurate cardiac output determinations by impedance plethysmography.

SUMMARY OF THE INVENTION

The catheter of the present invention comprises an elongated plastic tubular member having a plurality of lumens running the length thereof, the catheter body being sufficiently flexible that it may be routed through the vascular system and into the right ventricle of the heart. To assist in the catheter placement, a floatation device in the form of a balloon is located near the distal end of the catheter and may be inflated by a suitable fluid via one of the plural lumens and an appropriately positioned port extending through the wall of the catheter in the zone occupied by the balloon. Located a predetermined distance or length proximal from the distal end of the catheter are a series of surface electrodes in the form of conductive rings mounted on the exterior surface of the catheter body and extending in an axially spaced manner over a second predetermined length of the catheter. Each of the surface electrodes is connected to an appropriate electrical connector located at the proximal end of the catheter by way of wires which pass through a second lumen.

To provide an independent measure of forward flow, both to permit the verification of cardiac outputs determined by impedance plethysmography and for the quantitation of valvular regurgitation, thermal dilution capability may be included in the catheter. In order to accomplish this, a port is formed through the side wall of the catheter body proximally of the balloon, this port containing a thermistor-type sensor whose electrical leads extend the length of the catheter body via a further lumen. The thermistor can also be used for determining blood temperature upon demand. A still further port is located proximally of the most proximal one of the ring electrodes and communicates with yet another lumen, the proximal lumen. This lumen is used to measure right atrial pressure and for drug delivery. Also, cold saline may be injected at the proximal end of the catheter through this proximal lumen and out the port so as to be ejected into the right atrial chamber. Then, on the next contraction, a temperature change may be detected by the thermistor and by noting the temperature change, the cardiac output can be inferred, all as is well known in the art.

Located in the same lumen through which the cold saline is introduced, but distally to the proximal ejection port in the catheter side wall, are first and second stiffener members which are longitudinally spaced from one another by a short predetermined distance, with one such stiffener member being in the zone of the catheter spanned by the surface electrodes and the other stiffener member being proximal thereto. The spacing between the stiffener members allows the catheter to bend at an acute angle with the most proximal surface electrode being located in the apex of the right ventricle and the segment of the catheter bearing the more distal surface electrodes projecting upward through the right ventricle when the flow-directing balloon portion of the catheter is located within the pulmonarty outflow tract of the heart. Furthermore, the spacing between the stiffener members contained within the same lumen in the catheter permits the catheter to bend at an acute angle without kinking and occluding the catheter's plural lumens. Moreover, the routing of the catheter into and out from the right ventricale is such that there is minimal contact between the catheter body and excitable tissue. Hence, the occurence of catheter-induced PVCs may be reduced.

OBJECTS

It is accordingly a principal object of the present invention to provide a new and improved catheter for use in monitoring stroke volume.

Another object of the invention is to provide a catheter for use with stroke volume monitoring equipment that facilitates the measurements of cardiac output on a beat-by-beat basis.

Still another object of the invention is to provide, in a single catheter structure, means for conducting stroke volume measurements using two different techniques so that comparison and/or calibration can be performed.

Yet another object of the invention is to provide a right ventricular, flow-directed catheter having a series of axially aligned surface electrodes extending over a predetermined length proximally of the balloon such that when the balloon is guided into the pulmonary outflow tract, the portion of the catheter bearing the surface electrodes extends substantially the entire length of the right ventricle and remains substantially straight.

A yet further object of the invention is to provide a flow-directed catheter having spaced-apart stiffening members contained in the lumen thereof for causing the catheter to bend in a predetermined fashion proximate the apex of the right ventricle.

These and other objects and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE DRAWINGS

FIG. 1 is a drawing showing the preferred embodiment of the present invention;

FIG. 2 is a cross-sectional view taken along the line 2—2 in FIG. 1;

FIG. 3 is a cross-sectional view taken along the line 3—3 in FIG. 1;

FIG. 4 is a longitudinal cross-section view of the distal end portion of the catheter of FIG. 1;

FIG. 5 is a further longitudinal sectional view showing the manner in which a typical surface electrode is configured;

FIG. 6 is a cross-sectional view showing the manner in which the thermistor-type temperature sensor is disposed in the lumen of FIG. 1;

FIG. 7 is a drawing showing the construction of stiffener members used in the embodiment of FIG. 1;

FIG. 8 is an alternative stiffener member used in the embodiment of FIG. 1;

FIG. 9 shows the manner in which the stiffener of FIG. 7 is installed in the proximal lumen of the catheter of FIG. 1; and FIG. 10 is a sectional view of the heart showing the catheter of this invention installed in the right ventricle.

DESCRIPTION OF THE PREFERRED EMBODIMENT

Referring to FIG. 1, the diagnostic catheter of the present invention is seen to comprise an elongated tubular member 10 which is extruded so as to have a predetermined outer diameter which, for purposes of example only, may be about 2.28 mm and which is preferably formed from silicone rubber, polyurethane or some other suitable plastic which tends to be non-thrombogenic. With reference to the cross-sectional view of FIG. 2, there are a plurality of separate lumens 14, 16, 18, 20 and 22 extending the length htereof. For reasons which will become apparent from a continued reading of the specification, the lumen 14 is referred to as the inflation lumen, 16 the distal lumen, 18 the sensing electrode lumen, 20 the thermistor lumen, and 22 the proximal lumen. For a catheter 10 of the typical size set forth above, the inflation lumen 14 may be about 0.37 mm in diameter. The lumens 16 and 22 may each be approximately 0.81 mm in diameter. The thermistor lumen 20 may also be 0.51 mm, while lumen 18 is about 0.71 mm in diameter.

Bonded to the proximal end 24 of the extruded catheter 10 is a yoke member 26 which provides a means whereby various devices may be connected to the several lumens running through the catheter body 10. The yoke 26 is preferably molded from a thermosetting, medical grade plastic. With the aid of the cross-sectional view of FIG. 3 and the view of FIG. 1, there is shown a length of PVC tubing 28 which is adhesively bonded within the yoke 26 and a Luer lock 30 is affixed to the other end of the tube 28. Thus, fluid communication is established between the Luer lock 30 and the proximal lumen 22 (FIG. 2) of the catheter 10. As shown in FIG. 1 and as better seen in the enlarged view of FIG. 9, extending through the side wall of the tubular catheter 10 and communicating with the proximal lumen is a port 32. Thus, fluid communication is established from the Luer lock 30, through the tube 28 and the yoke 26, and through the proximal lumen 22 out through the port 32.

In a somewhat similar fashion, a tube 34, preferably formed from PVC, is terminated at its proximal end with a Luer lock 36. The other end is adhesively bonded into a bore in the yoke 26 leading to the distal lumen 16 (FIG. 2) which extends the entire length of the catheter body 10 and terminates in a distal port 38. Thus, fluid such as radiopaque dyes, drugs, etc. may be introduced through the Luer connector 36 and will flow through the tubing 34, the yoke 26 and the distal 16 to exit the distal port 38.

As can best be seen in the enlarged view of FIG. 4, the distal end portion of the catheter 10 is formed to a reduced diameter. Fitted over that end portion is a piece of expandable balloon tubing 40. It is bonded to the catheter body 10 at locations 42 and 44 with a suitable adhesive. Formed through the side wall of the catheter 10 in the zone spanned by the balloon member 40 is a port 46 which communicates with the inflation lumen 14. The inflation lumen runs the entire length of the catheter body and extends through the yoke 26 where a PVC tube 48 joins it to a Luer valve 50. Thus, when a fluid, under pressure, is introduced through the opened Luer valve 50, it flows through the tube 48, the yoke 26, the inflation lumen 14 and out the port 46 to inflate the balloon 40. By then closing the valve 50, the balloon can be retained in its inflated state.

Next, with reference to FIGS. 1 and 5, it can be seen that there are affixed to the outer surface of the tubular catheter 10, a plurality of ring-type surface electrodes 52, the most proximal ring being identified by numeral 52P and the most distal ring being identified by numeral 52D. For a catheter to be used with an adult heart, the ring electrode 52D may typically be disposed approximately 80 mm from the distal end of the catheter 10. The spacing between adjacent surface electrodes may typically be 10 mm, but it to be understood that an alternative spacing may be used, especially in pediatric operations.

With reference to FIG. 5, independently connected to each of the surface electrodes 52, 52D and 52P are insulated conductors, as at 54, which extend proximally through the sensing electrode lumen 18 and through a length of PVC tubing 56 to the individual connector pins (not shown) contained within the connector housing 58. This connector is adapted to be joined to the electronic circuitry used in the measurement of stroke volume using impedance pleysthmography.

Next, with reference to FIGS. 1 and 6, formed through the side wall of the tubular catheter 10 is an opening 60, and just below the opening 60 is a thermistor element 62 which is disposed within the thermistor lumen 20. Its electrical leads 64 extend down this lumen and through the yoke 26 and the PVC tubing 66 to a further electrical connector 68. A plug formed from silicone rubber adhesive is identified by numeral 70. Then, a plastic, such as polyurethane, having good heat conducting properties, is made to cover the opening 60 to prevent the ingress of blood and other body fluids.

Referring now to FIG. 9, it can be seen that a polyurethane potting adhesive plug 72 is injected into the proximal lumen at a location just distal of the proximal port 32 so as to block that lumen against any fluid flow therebeyond. The proximal lumen 22 continues distally of the plug 72, however, and disposed in this lumen are first and second stiffening members of the type shown in FIG. 7 of the drawings. The stiffening members are indicated generally by numeral 74 and comprise a stainless steel coil 76 surrounding a stainless steel core wire 78. The core wire 78 is welded at each end (80 and 82) to the surrounding coil wire 76. In the case of a catheter made in accordance with the preferred embodiment being described herein, the coil may be made from a 0.150 mm wire wound as a unifiler coil and preferably is fabricated from Type 304 stainless steel. The core wire may typically have a diameter of 0.355 mm and also may be Type 304 stainless steel. By welding the core wire to the coil on each end thereof, unraveling of the coil is precluded when the stiffener is subjected to tensile forces. The welded core wire also precludes penetration of the lumen walls.

As shown in FIG. 8, it is also contemplated that one end of the core wire 78 may be tapered as shown at end 80 thereof to thereby increase the relative flexibility of the stiffener member at that end. The purpose of this will become more apparent as the description proceeds. Irrespective of the type of stiffener member used, they may be approximately 0.815 mm in diameter and may have an overall length of approximately 10 cm.

Referring again to FIGS. 1 and 9, a first stiffener member 74 may be fed down the proximal lumen until positioned in the zone occupied by the spaced-apart surface electrodes 52 and identified by the bracket 84. Spaced proximally from the above-mentioned distal stiffener member is a second stiffener member which extends distally from the end of the potting adhesive plug 72 near the proximal port 32 (FIG. 9) in the zone identified by bracket 86. These two stiffener members, being located in the proximal lumen of the catheter 10 and spaced apart from one another by a short distance gives the catheter a tendency to bend in the zone between the two, but in such a manner that the catheter does not kink so as to occlude the lumen.

The surface electrodes 52 are crimped in place only after the stiffener member 74 has been fitted into the zone 84, and the crimping operation not only secures the ring electrodes to the outer surface of the catheter, but also tends to hold that stiffener member 74 in place.

OPERATION

Referring to FIG. 10, there is shown a sectioned view of a heart with the catheter of the present invention installed so as to facilitate the monitoring of the patient's stroke volume using right ventricular impedance pleysthmosgraphy. The catheter is installed by entering the patient's subclavean vien or a brachial vein and routing it through the superior vena cava into the right atrium and from there through the tricuspid valve into the right venitricle. At this point, an inflating fluid is applied under pressure to the inflation lumen, via the valve 50, and the fluid exits the port 46 (FIG. 4) to inflate the expander (balloon) 40. As blood is pumped from the right ventricle, the balloon 40 tends to be carried by the flow into the pulmonary outflow tract. Because of the first and second stiffener members, which are disposed in the proximal lumen downstream distally of the proximal port 32 and the relative dimensions of those stiffener members and the spacing therebetween, the catheter tends to bend at a point proximate the apex of the right ventricle, as illustrated in FIG. 10, with the segment 84 on which the surface electrodes are arrayed extending upwardly through the right ventricle. The proximal ring electrode 52P is located in the apex of the heart while the distal surface electrode 52D is at the entrance to the pulmonary outflow tract.

Once the catheter is so installed, stroke volume measurements can be taken using the technique set out in the Salo Application Ser. No. 773,048, filed Sept. 6, 1985, and entitled "METHOD AND APPARATUS FOR MEASURING VENTRICULAR VOLUME" (Now U.S. Pat. No. 4,674,575). Because the present invention is concerned with the physical construction of the catheter, it is deemed unnecessary to explain in detail how the stroke volume measurements are obtained. Those desiring an explanation of the impedance pleysthmography technique for measuring stroke volume can refer to the aforementioned application and to the publications referenced therein.

To be able to calibrate the stroke volume measurements, the catheter of the present invention also permits a measurement of cardiac output using the thermal dilution technique. As is well known to practitioners in the field, a cold saline solution may be injected through the proximal lumen via Luer lock 30 whereupon it exits the proximal port 32 which, as seen in FIG. 10, will be located in the right atrium. The temperature change occasioned by the flow of the cold saline diluted blood will be picked up by the thermistor element 60 exposed through the port 60 in the pulmonary outflow tract, and suitable instrumentation coupled to the electrical terminal 68 is used to convert that temperature change information to a stroke volume value for comparison with the stroke volume obtained using the impedance pleysthmography technique.

In using a catheter of the type described herein to measure relative stroke volume, a fewer number of sensing electrodes, e.g., four, positioned along the catheter body from the apex of the right ventricle to the pulmonic valve would be sufficient. Where absolute stroke volume is being assessed, however, an increased number of sensing electrodes, e.g., ten, is more appropriate. Furthermore, with the catheter designed for measuring absolute stroke volume, it is not required that provision be made for conducting thermal dilution measurements such that the thermistor sensor can be eliminated. It is important, however, that it be included where relative stroke volume measurements are to be obtained so that periodic correlations can be made.

Because of the inclusion of the stiffener members 74, the catheter does not tend to lay along excitable heart tissue and, hence, catheter-induced PVCs are minimized.

By using a stiffener member of the type shown in FIG. 8 with a tapered core wire 78 and by orienting that stiffener in the proximal lumen so that the tapered end of the stiffener member is pointing toward the balloon 40 in the zone 84 of the catheter, the ability of the catheter to snake around turns is ehnanced. This is particularly advantageous in pediatric use of the catheter.

Thus, there has been shown and described the design of a diagnostic coronary catheter which can be left in place over a period of hours and even days so that a variety of medical procedures and measurements may be carried out. One or more drugs may be injected into the heart cavity via the distal end port 38 and the effect of those drugs on cardiac performance can be monitored as previously described.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to equipment details and operating procedures, can be accomplished without departing from the scope of the invention itself.

What is claimed is:

1. A diagnostic catheter for use in measuring cardiac output in the right ventricular chamber comprising:
   (a) an elongated, multi-lumen, flexible member having a distal end and a proximal end, a first lumen extending the entire length of said member and terminating in a distal port, a second port extending through the side wall of said member at a location immediately proximate of said distal end of said flexible member and a second lumen extending from said proximal end of said member to said second port;
   (b) an expandable sleeve surrounding said member and spanning said second port, said sleeve inflatable by a fluid introduced into the proximal end of said second lumen;
   (c) a plurality of ring electrodes secured to the outer surface of said member at predetermined axial spacing including a distal ring electrode located a first predetermined distance proximal of said distal end of said flexible member, a proximal ring electrode located a second predetermined distance greater than said first predetermined distance from said distal end of said flexible member and a further plurality of intermediate ring electrodes disposed between said distal ring electrode and said proximal ring electrode;
   (d) a plurality of electrical conductors extending longitudinally through a third lumen in said flexible member from said proximal end of said flexible member and individually connected to separate ones of said plurality of ring electrodes;
   (e) a first stiffening member disposed in a fourth lumen in said flexible member and extending from said first predetermined distance to said second predetermined distance; and
   (f) a second stiffening member also disposed in said fourth lumen in said flexible member and extending from a location proximal of the proximal end of said first stiffening member for a third predetermined distance, the spacing between the opposed ends of said first and second stiffening members in said fourth lumen creating a zone in which said flexible member can bend without kinking the lumens of said multi-lumen flexible member, said first and second stiffening members positioning said proximal ring electrode at the apex of the ventricle of the heart, said distal ring electrode near the pulmonic valve and said intermediate ring electrodes out of contact with endocardial tissue.

2. The diagnostic catheter as in claim 1 and further including a fifth lumen extending from said proximal end of said flexible member and terminating in a third port formed through the side wall of said flexible member and located within said first predetermined distance; and a thermistor element exposed to heat conduction through said third port and having conductor means extending therefrom through said fifth lumen to the proximal end of said flexible member.

3. The diagnostic catheter as in claim 1 and further including a fourth port extending through the side wall of said flexible member and communicating with said fourth lumen at a location proximal of the proximal end of said second stiffening member.

4. The diagnostic catheter as in claim 1 wherein said first and second stiffening members each comprise a helical stainless steel coil having a strand of stainless steel disposed within the lumen of said coil, said strand being welded at each end to the opposed ends of said coil.

5. The diagnostic catheter as in claim 1 and further including a multi-terminal electrical connector connected to said plurality of electrical conductors.

6. The diagnostic catheter as in claim 2 wherein said third port containing said thermistor includes a plastic seal covering said thermistor, said plastic having a thermal conductivity property allowing said thermistor to detect a small temperature change rapidly.

7. The diagnostic catheter as in claim 1 and further including valve means connected to the proximal end of said second lumen of said flexible member.

* * * * *